United States Patent
Mereish et al.

(10) Patent No.: US 6,306,350 B1
(45) Date of Patent: Oct. 23, 2001

(54) WATER SAMPLING METHOD AND APPARATUS WITH ANALYTE INTEGRATION

(75) Inventors: Kay A. Mereish, Leesburg, VA (US); Michael R. Lewis, St. Charles, MD (US); John T. Stone, Fredericksburg, VA (US); Scott E. Lilienthal, Laurel, MD (US); Edward O. Gordon, Springfield; Claudia L. Randolph, Alexandria, both of VA (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 0 days.

(21) Appl. No.: 09/314,004

(22) Filed: May 19, 1999

(51) Int. Cl.⁷ ..................................................... G01N 1/14
(52) U.S. Cl. .................... 422/81; 73/863.21; 73/863.24; 73/863.25; 73/864.34; 210/445; 436/177
(58) Field of Search .............................. 436/177; 422/81, 422/67; 210/445; 73/863.21, 863.23, 863.24, 863.25, 864.34

(56) References Cited

U.S. PATENT DOCUMENTS

| | | |
|---|---|---|
| 2,348,806 | 5/1944 | Gillard et al. . |
| 3,512,393 | 5/1970 | Weiss . |
| 3,897,213 * | 7/1975 | Stevens et al. ................. 73/61.55 X |
| 3,956,940 | 5/1976 | Guild . |
| 3,969,925 | 7/1976 | Niskin . |
| 4,089,209 | 5/1978 | Grana et al. . |
| 4,166,392 | 9/1979 | Farnworth . |
| 4,270,922 * | 6/1981 | Kerfoot ................................ 422/53 X |
| 4,485,684 | 12/1984 | Weber et al. ....................... 73/863.12 |
| 4,545,957 * | 10/1985 | Vanhumbeeck et al. ............... 422/81 |
| 4,554,826 | 11/1985 | Barry ............................. 73/864.63 X |
| 4,871,662 | 10/1989 | Rosov ...................................... 435/30 |
| 4,978,506 | 12/1990 | Calderwood ........................... 422/73 |
| 5,024,952 * | 6/1991 | Alsop ..................................... 436/177 |
| 5,167,802 | 12/1992 | Sandstrom et al. .................. 210/134 |
| 5,441,071 | 8/1995 | Doherty et al. ........................ 137/15 |
| 5,478,526 * | 12/1995 | Sakai et al. ............................. 422/81 |
| 5,512,491 * | 4/1996 | Mekheri et al. ...................... 436/177 |
| 5,695,719 * | 12/1997 | Lyngaard et al. ....................... 422/81 |
| 5,834,633 * | 11/1998 | Davison ........................ 73/863.23 X |
| 5,837,192 * | 11/1998 | Dumschat ........................... 422/68.1 |
| 5,844,147 | 12/1998 | Fiedler et al. ..................... 73/863.21 |
| 5,910,448 * | 6/1999 | Atwater et al. ................. 73/61.41 X |
| 5,928,951 * | 7/1999 | Seshimoto et al. .................... 430/46 |
| 5,948,684 * | 9/1999 | Weigl et al. ............................ 430/52 |
| 6,007,775 * | 12/1999 | Yager ..................................... 422/57 |

FOREIGN PATENT DOCUMENTS

| | | | |
|---|---|---|---|
| 4133790A1 * | 4/1993 | (DE) ................................... 73/823 |
| 58-50462 * | 3/1983 | (JP) . |
| 58-202873 * | 11/1987 | (JP) ...................................... 436/62 |
| 9-285785 * | 11/1997 | (JP) . |
| 10-339724 * | 12/1998 | (JP) . |

OTHER PUBLICATIONS

Product Literature of American Sigma, Inc. 1996, month not given "Model 900 Portable Sampler Specifications", 2 pages.

* cited by examiner

Primary Examiner—Thomas P. Noland

(57) ABSTRACT

A method and apparatus of sampling a body of water in which discrete samples are successively withdrawn from a body of water and analyte is extracted from the respective samples while integrating the analyte which is extracted from successive samples. A filter unit in which male and female fittings may be locked together, and unlocked to allow replacement of filter membranes/screens discs or elements.

7 Claims, 5 Drawing Sheets

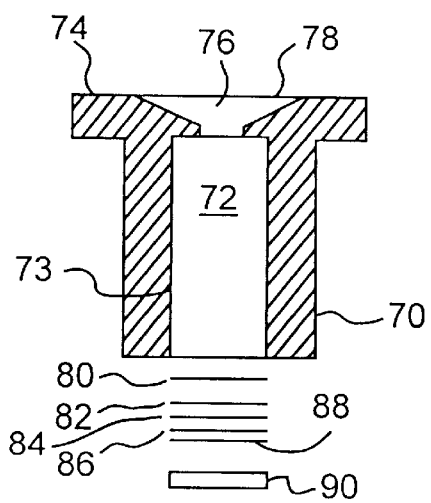
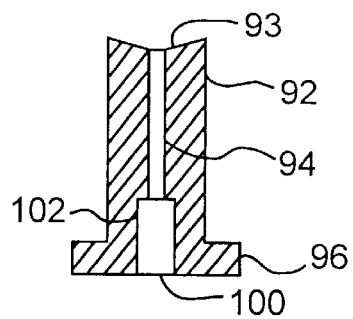
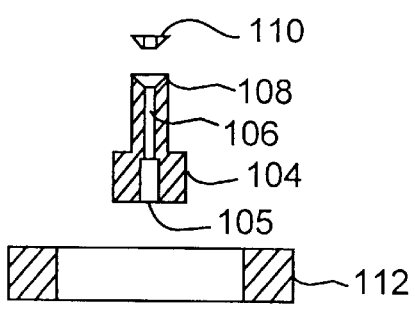
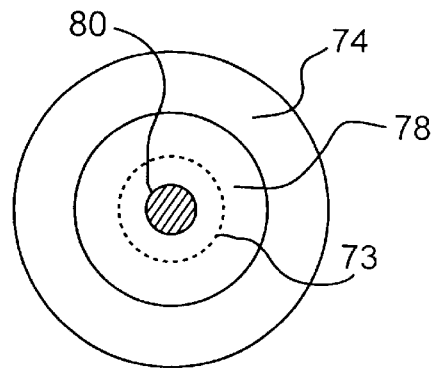
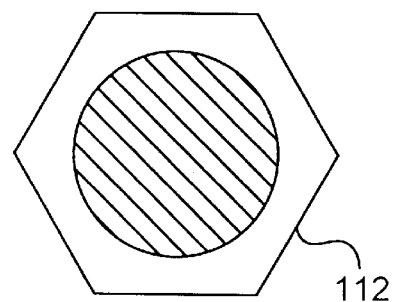
FIG. 4
FIG. 5
FIG. 6

WATER SAMPLING METHOD AND APPARATUS WITH ANALYTE INTEGRATION

FIELD OF THE INVENTION

The present invention is directed to a water sampling method and apparatus, and particularly to such a method and apparatus for extracting biological or chemical analytes from the water.

BACKGROUND OF THE INVENTION

Bacterial contamination of waterways, both in the United States and abroad is a continuing problem which frequently generates newspaper headlines. Any program to keep water clean is dependent on providing an effective monitor for water quality including low levels of microbial and chemical contaminants. While technologies are emerging for the rapid analysis of samples containing cellular and sub-cellular material such as DNA and RNA, the means for sampling the water to collect the biological and chemical fragments have not progressed as rapidly.

One prior art method, known as "grab sampling" is merely the collection of an instantaneous unit of water matrix in a sampling vessel such as a glass jar. However, a grab sample is often inadequate to characterize a dynamic water body such as a stream or river where flow patterns and content change rapidly and frequently.

While automatic devices exist for sampling water, these typically have the disadvantage of not being man-portable. One reason for this is that such devices frequently include one or more containers for storing sampled water, which add to the weight and space occupied by the device. Another disadvantage of some prior art devices is that they are designed to take only a single time-limited sample. In view of the changing conditions of rivers and streams over time, it is desirable to have a device which can take a large number of samples over a relatively long period of time (e.g. two weeks) without human intervention.

Still another disadvantage of some prior art is their need to use a high-pressure or high-capacity pump to generate the liquid flow demanded by the sampler cartridge. This requires generally higher voltage and ultimately higher power requirements not readily available by battery power alone. It is desirable to have a sampler capable of sampling in remote areas autonomously (i.e., without an external source of power).

U.S. Pat. No. 5,844,147 is directed to a water sampling apparatus in which a sample is collected at a relatively high flow rate and then is temporarily stored in a storage container under pressure before passing through a solid phase extraction device at a slower rate which corresponds to the flow tolerance of the extraction device. This enables a quantity of water to be sampled over a single limited time frame during which the storage container fills up. The apparatus does not include a backflush capability which would be necessary to keep the flow system clear for providing repetitive samples.

SUMMARY OF THE INVENTION

In accordance with a first aspect of the present invention, the above limitations of the prior art are overcome by providing a method of monitoring a body of water, comprising, successively withdrawing discrete samples of water from the body of water, and with an extraction device, successively extracting analyte from the respective discrete samples of water while integrating the analyte which is extracted from successive samples.

This allows successive samples to be taken over a relatively long time period to characterize dynamic water conditions, while conveniently integrating analyte at a single location.

In accordance with a further aspect of the invention, an apparatus for sampling water is provided in which the fluid transport system is matched with the flow characteristics of the extraction device. This enables a continuous flow through the extraction device over successive sampling cycles without the need for fluid storage. Since the apparatus does not include storage containers for sampled water, it is compact and lightweight enough to be man-portable.

In accordance with still a further aspect of the invention, a filter unit is provided comprised of locking/unlocking male and female fittings, which conveniently allows the filter screen/membrane to be varied, and replaced after each use if desired.

BRIEF DESCRIPTION OF THE DRAWINGS

The invention will be better understood by referring to the accompanying drawings, wherein:

FIG. 4 is an exploded cross-sectional view of a filter unit.

FIG. 5 is a top view of the filter unit of FIG. 5.

FIG. 6 is a plan view of the locking nut of FIG. 5.

DETAILED DESCRIPTION OF PREFERRED EMBODIMENTS

Figure 1:
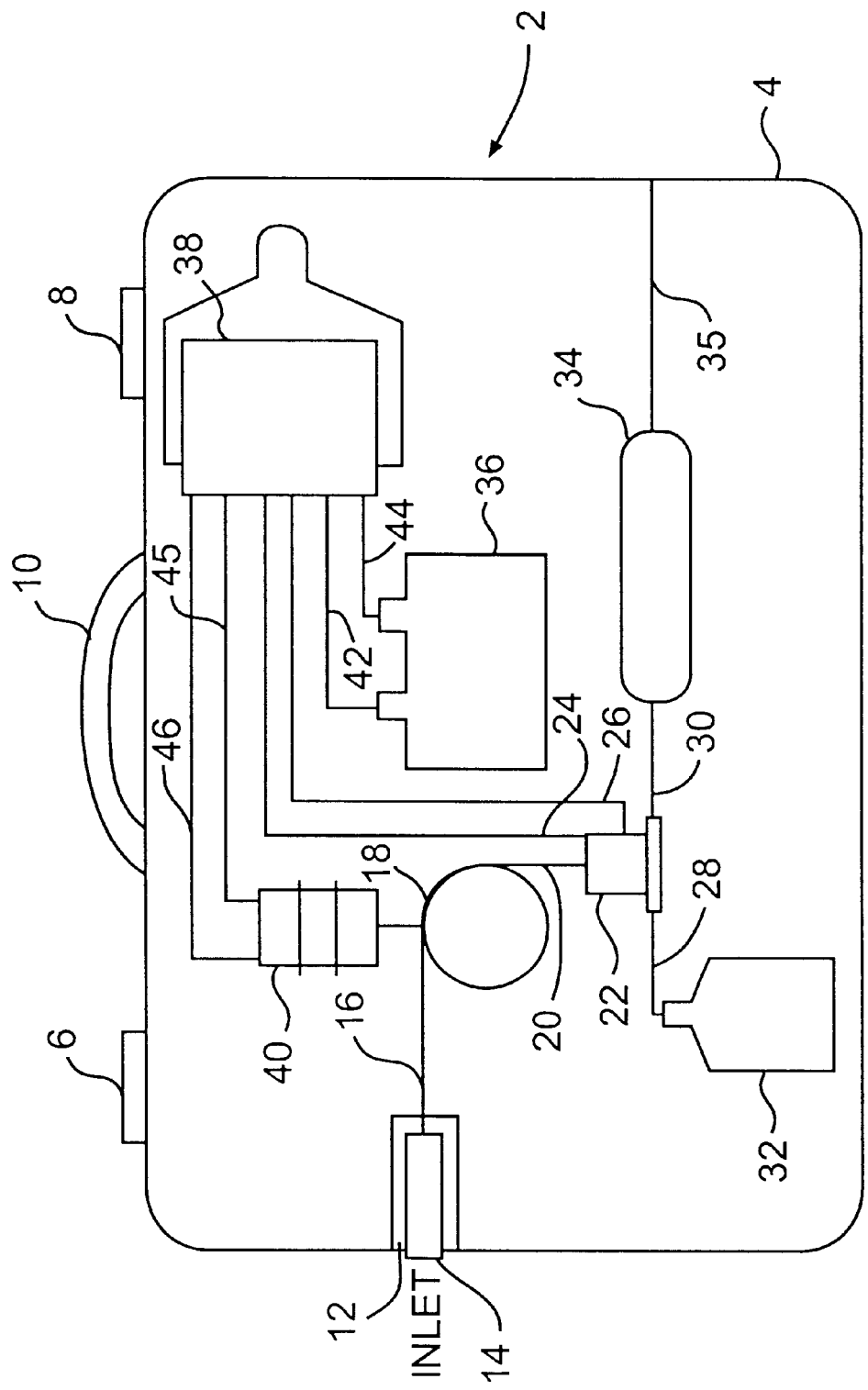
FIG. 1 shows an embodiment of the invention.

Referring to FIG. 1, an embodiment 2 of the water sampling apparatus of the invention is depicted. As discussed above, an advantageous feature is that the water sampler may be made man-portable. To this end, the apparatus is carried in a small carrying case or box 4 which is waterproof and has clasps 6 and 8, along with handle 10.

An inlet is formed in one side wall of the case in the form of a penetration 12 which may contain a PTFE fitting insert sealed to render it watertight. In the inlet is a pre-treatment filter unit 14, described in greater detail below, for removing interferences from the water matrix which is pumped through the apparatus. The pumping is accomplished by pump 18, which in the preferred embodiment is a peristaltic pump, capable of pumping in forward and reverse directions.

An electric motor 40 drives the pump, while tubing 16 leads from the filter unit to the pump and tubing 20 is between the pump and three way electrically controlled valve 22. The valve is in fluid communication with liquid container 32 through tubing 28, which serves to backflush the apparatus through the pre-treatment unit. The valve also communicates through tubing 30 with solid phase extraction device 34. The device 34 extracts analyte of interest from the water matrix, while the discharge flows through tubing 35 to an outlet which is rendered watertight.

The apparatus is controlled by electronics 38 which will be described in greater detail below. Briefly, the electronics is comprised of a programmable controller for causing the fluid flow transport system which is comprised of pump 18, pre-treatment unit 14, valve 22 and associated tubing to move water matrix through the extraction device 34 in predetermined repetitive cycles of selected duration. The apparatus is powered by battery 36, and is thus capable of autonomous operation.

The extraction device 34 may be comprised of a cartridge utilizing any desired solid phase media. The media may be selected to preferentially capture DNA, RNA and/or other biological or chemical molecules. Device 34 serves to concentrate and integrate the analyte over repetitive sampling cycles. It has enough capacity to capture the desired amount of analyte. The device is brought to the laboratory after the total sampling period and is eluted (emptied), after which the analyte is analyzed using chemical or biological laboratory procedures.

The invention further has capability to be programmed for a specific sampling situation. For instance, if a particular contaminant/organism is known to proliferate at night, the sampler may be programmed to sample during that time.

As mentioned above, an aspect of the invention is to successively withdraw discrete samples of water from which analyte is extracted, while integrating the analyte which is extracted from successive samples. This allows samples to be taken over a relatively long period of time so that changing water conditions are represented in the integrated analyte.

Figure 2:
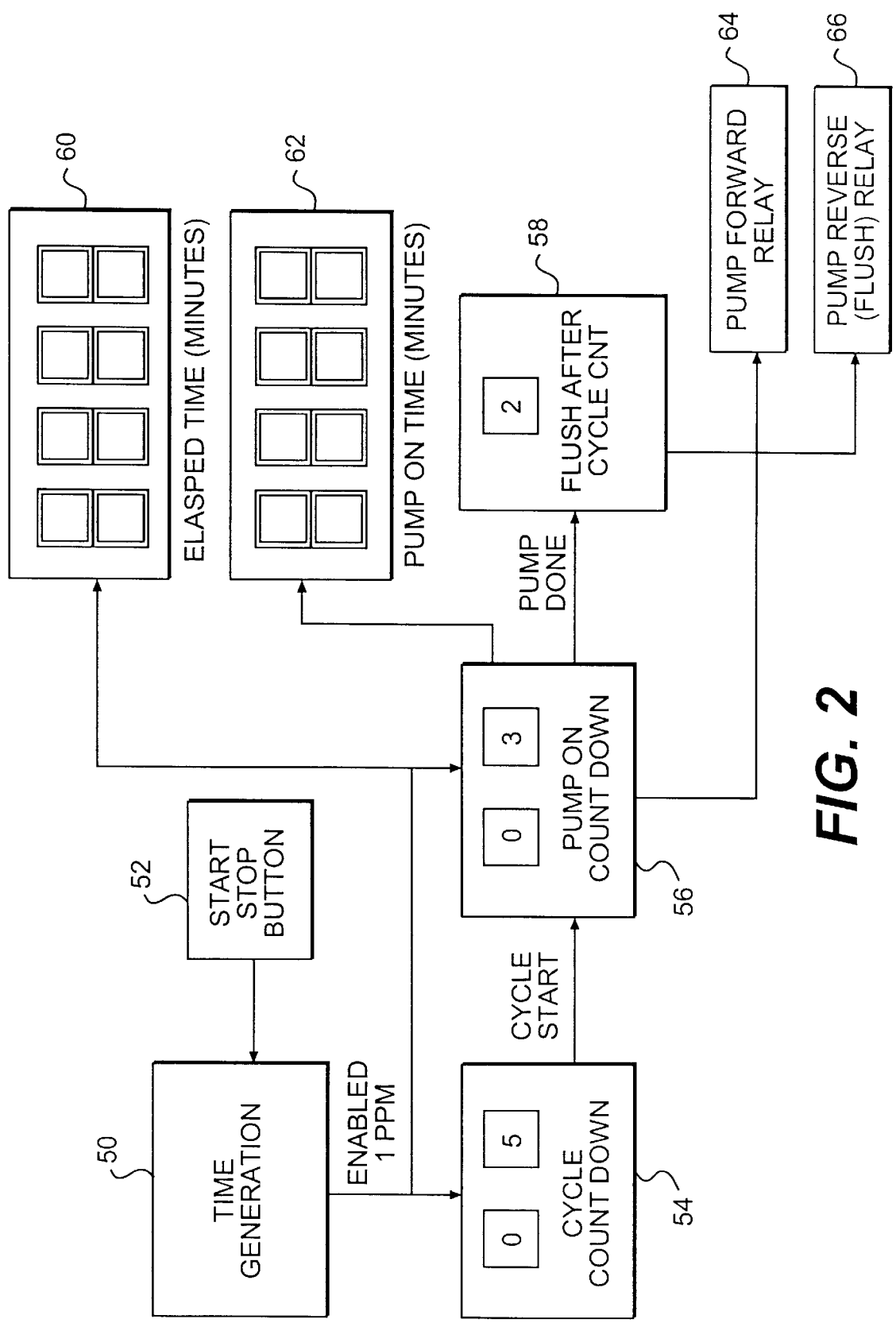
FIG. 2 is a block diagram of the controller.
Figure 3:
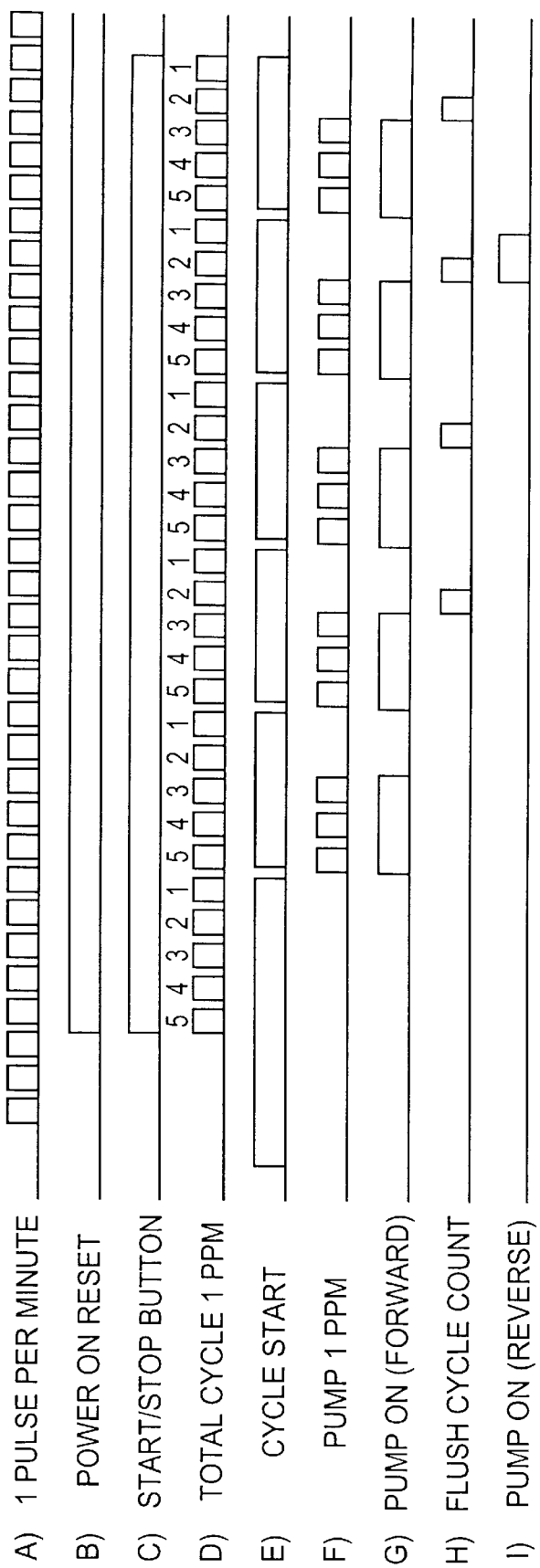
FIG. 3a to FIG. 3i depict the controller event timing.

FIG. 2 depicts a block diagram for an embodiment of the programmable controller which is indicated by electronics 38 in FIG. 1. Referring to FIG. 2, the controller is comprised of a clock 50 activated by a start/stop switch 52, and three counter circuits, 54, 56 and 58. Counter 54 is for the overall pump cycle, counter 56 is for the time per cycle that the pump is operating in forward mode, and counter 58 is for how often the pump flushes. Two output displays 60 and 62 consist of 4-digit LCD readouts summarizing the total elapsed time the device has been in operation and elapsed time of pump operation, respectively. The controller sends signals via relays 64 and 66 to a control unit for motor 40 for forward and reverse operation for the sampling and flushing cycles respectively.

The clock 50 generates clock pulses at regular intervals, e.g., one pulse per minute. The cycle down counter 54 counts the number of such pulses which are pre-programmed into the counter to constitute one pump cycle, and a cycle start pulse is emitted at its output at the beginning of each such cycle to activate the pump via counter 56 as well as pump forward relay 64 to begin pump operation. The duration that the pump is to be on during each cycle is pre-programmed into pump on down counter 56, also fed by clock 50, which turns the pump off after the selected number of clock pulses. The number of cycles after which the backflush is to periodically occur is pre-programmed into flush counter 58, which receives a pulse from counter 56 each time the pump goes off. The output of counter 58 is fed to the pump reverse relay 66 for operating the pump in the reverse direction, causing a backflush of liquid (such as deionized water) in reservoir 32 through the pre-treatment unit 14 (or through the entire system if desired).

As a non-limiting example, programming the apparatus includes first setting the total cycle time from 1 to 99 minutes (pulses). The pump on time is then set from 1 minute to the total cycle time. Then, the cycle to flush on is set. If the settings are 5, 3, and 2, then the pump will run for 3 minutes every 5 minutes with a flush cycle after the completion of every 2 main cycles. The system may be configured so that no pump activity happens on the initial cycle, when time is provided to place the apparatus. Also, the apparatus may be arranged to shut down if battery voltage drops below a set limit, thereby stopping the sampling with the displays showing the elapsed time at shut down and the minutes of pumping to that point. The timing diagram illustrating the above example (wherein the flush time is set to approximately 45 seconds) is shown in FIGS. 3a to 3i.

A feature of invention is that the total time of operation of the pump is indicated by display 62. From this, with a means of calculating the number of pump rotations, the total volume of water sampled can be easily calculated. This obviates the need for more complicated equipment to measure sample volume. Other methods of flow measurement are also possible.

As described above, an aspect of the invention is that the need for storage containers for the water matrix is obviated by matching the fluid transport system with the flow characteristics of the extraction device so that a continuous flow without fluid storage is achieved through the device over successive sampling cycles.

The invention will be illustrated herein in connection with a specific analyte extraction device and a specific pump, although it is to be understood that the invention covers such devices generally and the particular devices depicted are for purposes of illustration only. In fact, the specific devices depicted may be suitable only for certain applications while other devices with different characteristics may be preferred for other applications.

A graph or relationship of flow velocity in cm/hr vs. pressure for the extraction device used may be derived or obtained from the manufacturer. Pressure losses vary with flow and include frictional losses through the tubing as well as pressure drop due to the filtration and the collecting apparatus. It was estimated that, at the operating flow rates, the system pressure losses are minor for most components except the extraction device itself unless severe plugging of the filtration system occurs. The pressure drop across the extraction device depends on the size of the column and the packing.

Given the size of column and the flow range, the above-mentioned graph or relationship can be used to estimate the performance requirements of the pump. Such relationship would typically be a velocity-pressure relationship independent of column size. To relate pressure and flow, the cross-sectional area of the specific column may be used to convert velocity into a volumetric rate.

The illustrative extraction device is the DEAE 650S resin by Toyopearl which uses a methacrylic polymer phase material. The particular device (also called a "column") used had a 7.5 mm diameter and a 8.5 cm length.

The pump should be capable of overcoming the pressure losses through the unit over the entire range of flow. The specifications of the illustrative column reveal that it is designed to operate most effectively at 1 ml/min and can operate up to 2.5 ml/min for normal operation. From a table which was developed relating to velocity, flow(ml/min), and pressure drop, it was determined that the pressure that the pump should be capable of sustaining would range from zero to 36 psi.

The pump chosen, capable of attaining such pressures was a peristaltic pump having an integral variable frequency drive controller for controlling speed and direction of rotation. The flow rate is altered by changing rotational speed as well as by changing the diameter of tubing running through the pump. A specific pump for purposes of illustration, is the Proflex™ Series 710 Mini-Peristaltic Pump having a maximum flow capacity of up to 58 ml/min depending on the diameter (ID) of internal tubing, corresponding to a rated top speed of 93 RPM.

Testing the pump with distilled water and 1/32-inch inside diameter tubing, and the filtration system (but not the column) revealed that a pump speed of 30 rpm produced a flow of 0.8 ml/min. while a pump speed of 53 rpm produced a flow of 1.2 ml/min. Given that the optimum collection flow rate for the column of the example is 1 ml/min, such a pump output is consistent with column requirements. If pump output is lower than desired, the tubing diameter and/or pump speed may be increased to achieve a flow system that moves water matrix through the extraction device continuously without storing water.

Figure 7:
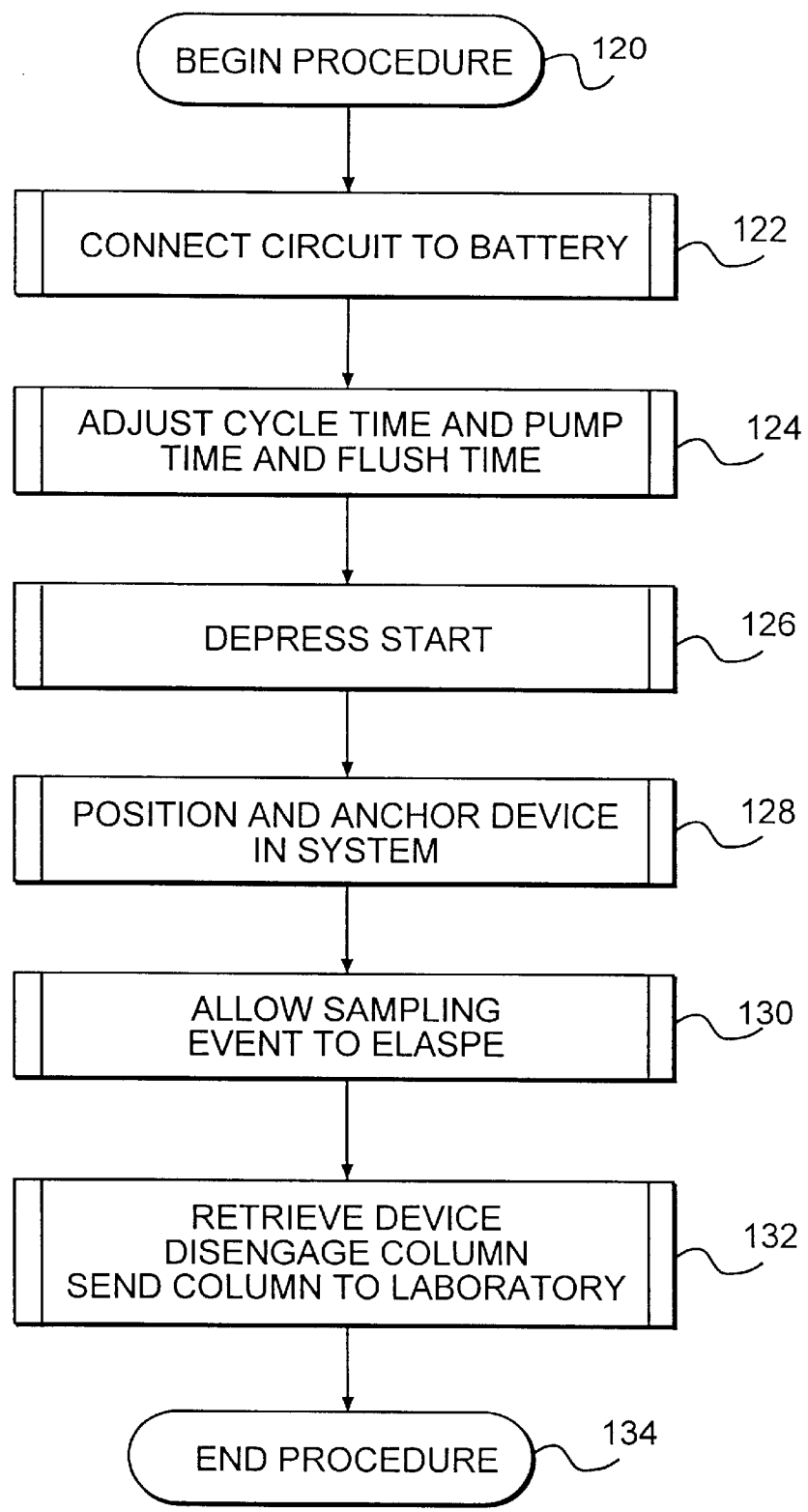
FIG. 7 is a flow diagram for operating a sampling apparatus in accordance with an embodiment of the invention.

A further feature of the invention is the specific pre-filter unit, which is shown in FIGS. 5 to 7. The fluid must be pre-treated to remove solids and other interferences that will cause reduced collection efficiency by the sampler collection cartridge. The structure of the pre-filter allows the filter membrane/screen to be varied and minimizes dead space. The filter unit may be used with the disclosed water sampler or with other fluid samplers.

Referring to FIG. 5, a filter is shown having a female fitting 70 in the form of a hollow cylinder, which has a fluid intake opening 76 defined by a tapered side wall 78. A series of filter screen/membranes having progressively finer openings 80, 82, 84, 86 and 88, is disposed against the inside of upper end of the fitting in the Figure. A rigid porous frit 90 is disposed against the membranes, all of the membranes and disc being in contact with each other. A male fitting 92 in the shape of a cylinder having an axially extending fluid passageway 94 is pushed up against the filter media. Opening 100 accommodates compressive fitting 104, which is for interfacing with tubing which is inserted in opening 105. The outside of shoulder 96 of male fitting 92 is threaded, as is locking nut 112 (shown in plan view in FIG. 7) which is tightened to secure the membranes/screens tightly in place. The nut may be opened to replace or vary the filter membranes/screens.

In the operation of the filter, fluid is drawn in through the intake 76 of the female fitting. Flow enters through the top recessed aperture, wherein the recessed portion serves to lessen dead volume in the device. As flow enters the device it immediately passes a series of successively finer filter membranes starting with a screen 80 for removing large debris such as stones and plant material. Successively finer mesh and membrane filters (82, 84, 86 and 88) remove finer and finer particulate matter without removing the analyte from the matrix. The flow rate through the surface area is such that an excessive pressure drop across the filter media is not encountered. Silver wool may be placed between the screen 80 and the membrane filter 82 for the control of bacterial growth. The invention is intended to have the capability of operating over periods of hours to weeks and to collect analytes relating to microbial activity. Bacterial growth on the filter must be inhibited. This accompanied via the silver. The frit 90 is porous and made of sintered stainless steel or TFE. The frit presses the filters against the openings of fitting 70 by the insertion of the male connector fitting 92. This has matching threads to fitting 70 and is screwed in to provide a seal between it and the frit 90. The male connector fitting has a concave end 98 which causes a small space to exist between it and all of the surface area of the frit except for the outer circumferential portion. Fluid is drawn through the frit and collects in this space where it continues through the hollow center of the male connector fitting. A ferrule 110 and compression fitting 104 are threaded and inserted into the female end of the male connector fitting 94. The (e.g. TFE) Tubing enters and is held securely by the ferrule and compression fitting combination. Flow continues through the tubing to the rest of the sampler. The overall flow system may be configured to allow backflushing through the filter to clear it of debris.

As mentioned above, taper 78 of the female fitting minimizes dead space and promotes the flow of fresh rather than stale water matrix into the sampler. Taper 98 of the male fitting ensures that flow emanates from the entire surface area of the frit 90.

A flow chart depicted in FIG. 8 illustrates the use of the water sampling apparatus. The procedure is begun (block 120) by connecting the circuit to battery 36 (block 122). The cycle time, pump time, and flush time are then programmed in the respective counters (block 124) after which the start switch 52 is activated (block 126). The sampler is then positioned and anchored in the stream or other body of water (block 128) and is left alone to allow the sampling events to elapse (block 130). The sampler is then retrieved, the analyte extraction device is removed and sent to the laboratory for being analyzed (block 132), whereupon the procedure is ended (block 134).

There thus have been described an improved method and apparatus for sampling water as well as an improved filter unit. It should be understood that the invention has been described in connection with illustrative embodiments, and that variations falling within the spirit and scope of the invention may occur to those skilled in the art. Thus, the invention is to be construed in accordance with the following claims.

We claim:

1. A water sampling apparatus, comprising,
   an intake for inletting water to be sampled,
   a fluid flow transport system including a pump capable of moving such water from the intake through a downstream location,
   a programmable controller for causing the fluid flow transport system to repeatedly move discrete water samples from the intake through the downstream location, and
   an extraction device at the downstream location for extracting said analyte from the discrete water samples which pass through and for integrating the analyte which is extracted from successive samples,
   wherein the programmable controller variably controls both the pump cycle, which defines those times at which activation of the pump begins to commence movement of respective discrete samples, and the duration during each such cycle that the pump operates.

2. The apparatus of claim 1 which includes only a single extraction device.

3. The apparatus of claim 2 further including means for periodically backflushig a fluid through at least part of the fluid flow transport system to avoid blockages and ensure that a large number of fresh samples may be moved to the extraction device.

4. The apparatus of claim 3 further including means for visually indicating the total time during which the fluid transport system has moved fluid samples from the inlet through the extraction device.

5. The apparatus of claim 3, wherein the programmable controller also controls the means for backflushing so as to cause the backflushing to occur periodically in correspondence with a pre-selected number of pump cycles.

6. The apparatus of claim 5 wherein the fluid transport system includes a filter unit.

7. A water sampling apparatus, comprising, an intake for inletting water to be sampled, a fluid flow transport system capable of moving such water from the intake through a downstream location, a controller for causing the fluid flow transport system to repeatedly move discrete water samples from the intake through the downstream location, a single extraction device at the downstream location for extracting analyte from the discrete water samples which pass through and for integrating the analyte which is extracted from successive samples, means for periodically backflushing a fluid through at least part of the fluid flow transport system to avoid blockages and ensure that a large number of fresh samples may be moved to the extraction device, means for visually indicating the total time during which the fluid transport system has moved fluid samples from the inlet through the extraction device, wherein the fluid flow transport system includes a pump, and wherein the controller comprises a programmable controller for variably controlling both the pump cycle, which defines the periodic times at which activation of the pump begins, and the duration during each such cycle that the pump operates, wherein the fluid flow transport system is matched to the flow characteristics of the extraction device so that the water is moved from the intake to the extraction device without storing the water, and wherein the fluid transport system includes a filter unit which comprises, a female fitting in the shape of a hollow first cylinder having a fluid intake opening at a first end and having a second end, a filtering means disposed against the first end, a male fitting in the shape of a second cylinder having a body in which there is an axially extending fluid passageway and having a first end for abutting the filtering means and a second end at which there is a shoulder having a greater diameter than the body for abutting the second end of the female fitting, the shoulder having threads around its periphery, and a threaded locking nut for cooperating with the threads on the shoulder of the male fitting for allowing the male fitting to be locked in the female fitting and also to be opened to allow replacement of the filtering means.

\* \* \* \* \*

UNITED STATES PATENT AND TRADEMARK OFFICE
CERTIFICATE OF CORRECTION

PATENT NO. : 6,306,350 B1
DATED : October 23, 2001
INVENTOR(S) : Mereish et al.

It is certified that error appears in the above-identified patent and that said Letters Patent is hereby corrected as shown below:

<u>Column 6,</u>
Line 46, the word "said" should be deleted.

Signed and Sealed this

Seventh Day of May, 2002

*Attest:*

JAMES E. ROGAN
*Attesting Officer*   *Director of the United States Patent and Trademark Office*